(12) United States Patent
Pomfrett et al.

(10) Patent No.: US 8,088,076 B2
(45) Date of Patent: Jan. 3, 2012

(54) NERVOUS SYSTEM MONITORING METHOD

(75) Inventors: Christopher John Douglas Pomfrett, Sandbach (GB); Hugh McCann, Stockport (GB)

(73) Assignee: The University of Manchester, Manchester (GB)

(*) Notice: Subject to any disclaimer, the term of this patent is extended or adjusted under 35 U.S.C. 154(b) by 261 days.

(21) Appl. No.: 10/553,745

(22) PCT Filed: Apr. 13, 2004

(86) PCT No.: PCT/GB2004/001565
§ 371 (c)(1),
(2), (4) Date: Oct. 18, 2005

(87) PCT Pub. No.: WO2004/093679
PCT Pub. Date: Nov. 4, 2004

(65) Prior Publication Data
US 2006/0189883 A1   Aug. 24, 2006

(30) Foreign Application Priority Data
Apr. 22, 2003 (GB) ................................. 0309049.5

(51) Int. Cl.
*A61B 5/05* (2006.01)
(52) U.S. Cl. ......... 600/558; 600/559; 600/547; 600/554
(58) Field of Classification Search ................... 600/547, 600/554, 558, 559
See application file for complete search history.

(56) References Cited

U.S. PATENT DOCUMENTS

| | | | | |
|---|---|---|---|---|
| 4,421,122 A * | 12/1983 | Duffy | ........................... | 600/544 |
| 4,862,359 A * | 8/1989 | Trivedi et al. | ................. | 600/544 |
| 5,143,081 A | 9/1992 | Young et al. | | |
| 5,638,825 A * | 6/1997 | Yamazaki et al. | ............ | 600/544 |
| 5,919,142 A * | 7/1999 | Boone et al. | ................... | 600/547 |
| 6,826,426 B2 * | 11/2004 | Lange et al. | ................... | 600/544 |
| 2002/0091335 A1* | 7/2002 | John et al. | ..................... | 600/544 |
| 2003/0009111 A1 | 1/2003 | Cory et al. | | |
| 2003/0032889 A1* | 2/2003 | Wells | ............................ | 600/546 |
| 2003/0163060 A1* | 8/2003 | Maddess et al. | .............. | 600/544 |

(Continued)

FOREIGN PATENT DOCUMENTS

| | | |
|---|---|---|
| DE | 101 04 153 A | 6/2002 |
| DE | 10104153 A1 | 6/2002 |

OTHER PUBLICATIONS

Polydorides. et al. ("Krylov Subspace Iterative Techniques: on Detection of Brain Activity with Electrical Impedance Tomography," IEEE Transactions on Medical Imaging, vol. 21 No. 6, Jun. 2002).*

(Continued)

*Primary Examiner* — Max Hindenburg
*Assistant Examiner* — Michael C Stout
(74) *Attorney, Agent, or Firm* — Nixon & Vanderhye PC

(57) ABSTRACT

A method for monitoring the response of a nervous system of a body to a stimulus. The method comprises collecting a set of voltage measurements between selected areas on a surface of the body while current is being passed between selected regions of the surface of the body. The set of voltage measurements is collected over a predetermined measurement period, the predetermined measurement period is initiated at a predetermined time after application of the stimulus, and the collected voltage measurements are compared with reference to determine normal or abnormal response of the nervous system.

22 Claims, 3 Drawing Sheets

U.S. PATENT DOCUMENTS

2004/0079372 A1\* 4/2004 John et al. ............. 128/204.18
2006/0036152 A1\* 2/2006 Kozel ........................ 600/410

OTHER PUBLICATIONS

Vauhkonen et al. ("A Kalman Filter Approach to Track Fast Impedance Changes in Electrical Impedance Tomography," IEEE Transactions on Biomedical Engineering, vol. 45, No. 4, Apr. 1998).\*

Holder, "Impedance Changes During the Compound Nerve Action Potential:Implications for Impedance Imaging of Neuronal Depolarisation in the Brain", Medical and Biological Engineering and Computing, Peter Peregrinus Ltd., Stevenage, GB, vol. 30, No. 2, Mar. 1, 1992, pp. 140-146.

Holder, "Impedance changes during the compound nerve action potential: implications for impedance imaging of neuronal depolarization in the brain", Medical and Biological Engineering and computing, vol. 30, No. 2, Mar. 1, 1992, pp. 140-146, XP000271685.

International Search Report of PCT/GB2004/001565, mailed Aug. 6, 2004.

Ph.D. Thesis by Nick Polydorides (Mar. 11, 2003).

\* cited by examiner

NERVOUS SYSTEM MONITORING METHOD

CROSS-REFERENCE TO RELATED APPLICATIONS

This application is the US national phase of international application PCT/GB2004/001565 filed 13 Apr. 2004 which designated the U.S. and claims benefit of GB 0309049.5, dated 22 Apr. 2003, the entire contents of each of which are hereby incorporated by reference.

The present invention relates to a method for monitoring the response of a nervous system of a body to a defined stimulus, such as a flash of light before a subject's eyes or an audible sound adjacent to a subject's ears, or another event or sequence of events.

BACKGROUND

1. Technical Field

There is a well-known requirement for a method capable of imaging the activity of a nervous system such as a human brain which is sufficiently fast to capture neural activity with sub-second resolution. For example, Susan Greenfield, a professor of pharmacology at Oxford University, England, giving the Andrew Olle Memorial Trust lecture in Sydney, Australia in May 2000 stated that "I think that there is the plausible prospect in this century of being able to devise very good imaging techniques that enable us to catch that which we can't catch at the moment because the imaging techniques are too slow". The present invention is concerned with delivering a method which is capable of imaging the human brain to sub-second resolution.

2. Related Art

As described by Pomfrett C. J. D. and Healy T. E. J. (1995), "Awareness and the Depth of Anaesthesia", Healy T. E. J and Cohen P. J. (eds) "A Practice of Anaesthesia", Edward Arnold, pages 864-878, it is well known that activity within the human brain can be monitored using standard EEG approaches. For example auditory, visual and somatosensory evoked responses can be generated which show that there is a latency after the occurrence of a stimulating event such as an audible sound or a light flash before sensory pathways in the brain respond. Typically there is a delay of at least several tens of milliseconds after a stimulating event before the evoked response can be detected by EEG equipment. Furthermore, although EEG equipment is capable of picking up signals showing that some response has been generated, the location of the source of such signals within the brain cannot be accurately determined from the detected signals.

It is known to use MRI and PET techniques to produce images of cerebral activity, but such techniques respond to haemodynamic and/or metabolic recovery processes which occur over time periods of typically many seconds or minutes and cannot therefore be used to image short term neural activity.

Electrical impedance tomography (EIT) has also been proposed as a method of imaging neurological functions within a body. U.S. Pat. No. 5,919,142 describes various EIT systems which have been proposed for measuring changes in impedance taking place within the brain and using those measurements to image the progress of information along circuits within the brain. It is stated that the brain may be stimulated by for example a visual signal and EIT images subsequently reconstructed for each millisecond or so of the recording "window", thus enabling the resultant action potential processes to be tracked along their pathways in the subject's brain. Although such a theoretical reconstruction to a resolution of milliseconds is discussed, it is conceded in U.S. Pat. No. 5,919,142 that there is no established technique to permit accurate imaging of neuronal depolarisation with millisecond or sub-millisecond time resolution. It is stated that impedance changes associated with action potentials are generally very small and very rapid and the impedance of the tissue as a whole which is interposed between locations at which impedance measuring electrodes must be positioned may not change in proportion to changes in local action potentials.

Individual impedance measurements (or voltage measurements during current injection) take a finite length of time, typically measured in milliseconds, and in order to build up a sufficient number of impedance measurements to enable the generation of a single image of local impedance distributions within the brain a number of individual impedance measurements must be taken. Typically therefore it takes a few hundred milliseconds to collect sufficient impedance measurements to produce a single image of the brain, although it is feasible to measure voltages in parallel during current injection, thus reducing the measurement period to a few tens of milli-seconds.

A further problem encountered with EIT systems when used for brain imaging is that changes of impedance resulting from neural activity within the brain are thought to be relatively small, for example between 0.1 and 1% of baseline impedance. If true, this makes it very difficult to distinguish impedance fluctuations resulting from changes in neural activity from background noise. The approach suggested in U.S. Pat. No. 5,919,142 seeks to improve sensitivity to changes in impedance resulting from neural activity by taking a first set of impedance measurements whilst a first electrical input signal is being applied to the brain for a period of for example 100 milliseconds or more, taking a second set of impedance measurements when a second electrical input signal that is the reverse of the first is applied to the brain, calculating the difference between the two sets of measurements, and generating an image on the basis of the calculated difference. The application of the first and second input signals can be synchronised with the application of separate stimulus signals to the body. The problem with this approach is that there is a 100 millisecond delay between the generation of the two sets of signals which are compared so as to generate the data from which an image is subsequently generated. It is quite clear therefore that such a system cannot be sensitive to changes in impedance resulting from cerebral activity occurring over periods of only a few milliseconds.

U.S. Pat. No. 5,919,142 dates from a priority date of Jun. 22, 1995. Since that date the same research group has continued with research into the use of electric impedance tomography for studying human brain activity. This is indicated by the paper "3-Dimensional Electrical Impedance Tomography of Human Brain Activity", Tidswell T., Gibson A., Bayford R. H. and Holder D. S., Neuro Image 13, 283-294 (2001). That paper describes the use of EIT to detect local changes in cerebral blood flow and blood volume. The data measurement for each impedance image was recorded over a period of 25 seconds. Before recording measurements, the neural stimulation process was initiated and remained active for several minutes. It is stated that reproducible impedance changes of about 0.5% lasted from 6 seconds after the onset of a stimulus to 41 seconds after stimulus cessation. The described system was however looking at the side-effects of brain activity, that is changes in blood flow and blood volume, rather than the neurological activity of which such changes are merely side effects. Furthermore, although some interesting results were generated, the paper itself concedes that problems of low resolution and reconstruction error remain which must be overcome if EIT is to be used as a fast neuro imaging tool with clear clinical applications. It is stated that a faster EIT system is being tested which will allow more measurements to be made per image but however many measurements are made, it still cannot be expected that the above technique will be sensitive to neuronal or synaptic phenomena occurring over a period of for example only one or a few milliseconds.

It is an object of the present invention to obviate or mitigate at least one of the problems outlined above.

BRIEF SUMMARY

According to a first aspect of the present invention, there is provided a method for monitoring the response of a nervous system of a body to an applied stimulus, comprising applying the stimulus, and collecting a set of voltage measurements between selected areas on a surface of the body whilst current is being passed between selected regions of the surface of the body, wherein the set of voltage measurements is collected over a predetermined measurement period, the predetermined measurement period is initiated a predetermined time after application of the stimulus, and the collected voltage measurements are compared with reference measurements to determine normal or abnormal response of the nervous system.

If a single set of measurements is taken, that set may be compared with predetermined data to assess neurological behaviour. If a series of sets of measurements are taken, neurological behaviour may be assessed by comparing different sets, and images representative of that behaviour may be generated.

The stimulus may be applied by the system, or alternatively may occur spontaneously. Occurrence of the stimulus may be detected, and this detection may start computation of the predetermined time. The stimulus may be a feature of an environment in which the body is located.

According to a second aspect of the present invention, there is provided a method for monitoring the response of a predetermined part of a nervous system of a body to an applied stimulus, comprising identifying the predetermined part of the nervous system, applying the stimulus, passing current between selected regions of the surface of the body, and collecting a set of voltage measurements between selected areas on the surface of the body, wherein the said regions and/or areas are selected on the basis of a neurological model of the nervous system and the applied stimulus such that sensitivity of the derived impedance measurements to changes in the predetermined part of the nervous system is maximised.

For example, if activity of the Lateral Geniculate Nucleus (LGN) is of interest, current may be passed between regions at the front and rear of the head to maximise the effect of activity in the LGN on the voltage measurements.

BRIEF DESCRIPTION OF THE DRAWINGS

Embodiments of the present invention will now be described, by way of example, with reference to the accompanying drawings, in which.

DETAILED DESCRIPTION OF EXEMPLARY EMBODIMENTS

Figure 1:
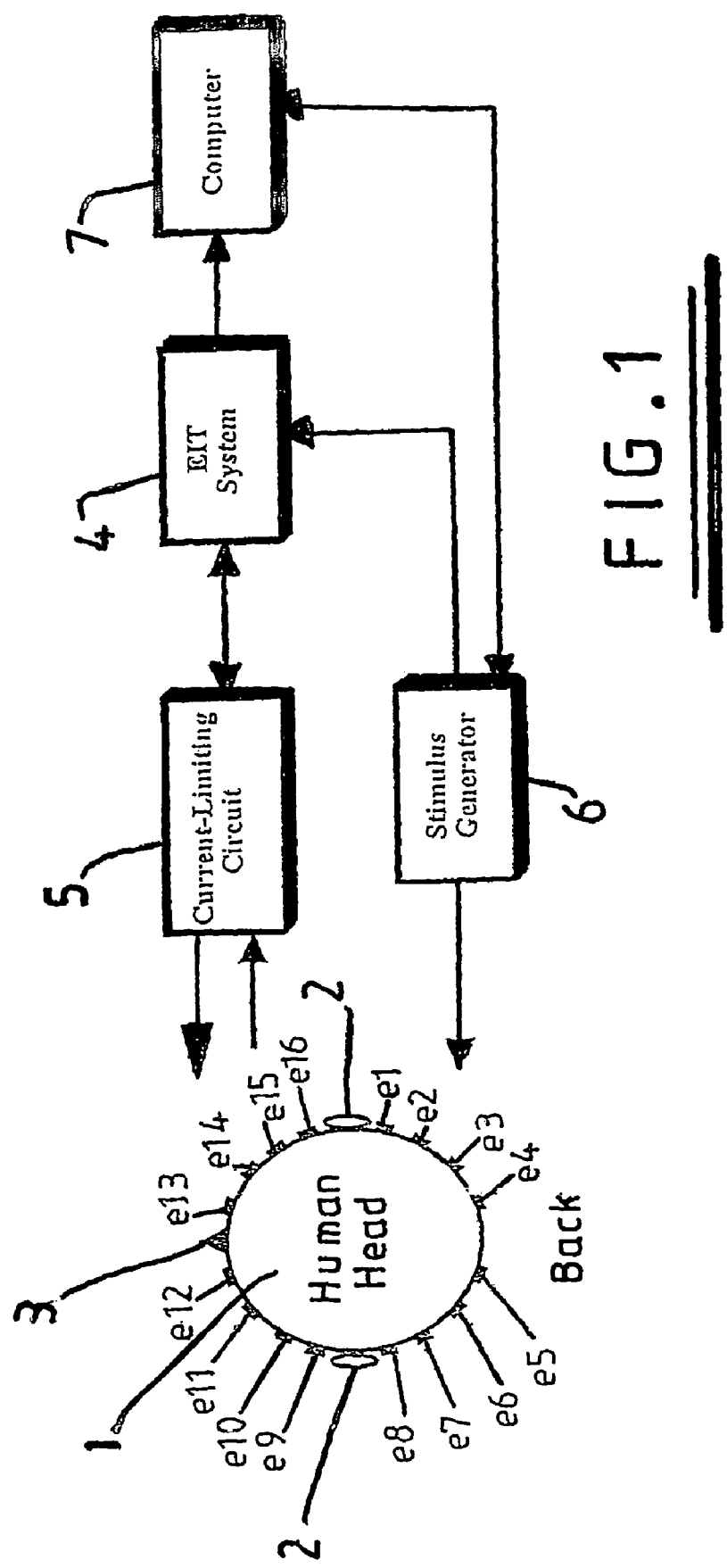
FIG. 1 is a schematic representation of an apparatus used in accordance with the method of the present invention.

FIG. 1 illustrates an apparatus for putting the invention into effect. A subject's head 1 has adhered to it sixteen electrodes e1 to e16 distributed in a plane around the head. In some circumstances it may be preferred to have a non-planar distribution of electrodes as described in Polydorides N., Lionheart W. R. B., and McCann, H.: "Krylov Subspace Iterative Techniques: On the detection of brain activity with electrical impedance tomography" IEEE Transactions on Medical Imaging, Volume 21, No 6, June 2002 pages 596-603. The subject's ears 2 and nose 3 are schematically illustrated to indicate the orientation of the subject's head. Calibrated headphones (not shown) are provided to deliver an auditory evoked response (AER) stimulus to the subject's ears and goggles (not shown) are provided which include light emitting diodes for generating a visually evoked response (VER) stimulus. Each of the sixteen electrodes is a silver-silver chloride EEG electrode of type, which present a relatively small contact impedance in the scalp.

An EIT system 4 is provided to deliver current to selected pairs of electrodes via a current limiting circuit 5 and to perform voltage measurements between other selected pairs of electrodes. A stimulus generator 6 also provides an input for the EIT system 4 such that EIT measurement can be effected at appropriate times relative to application of a stimulus. A computer 7 is provided to control the overall operation of the system and to log experimental results.

The equipment illustrated in FIG. 1 is essentially conventional and will not therefore be described in further detail here. Characteristics of such equipment are well known and details may be derived for example from the documents referred to above.

Figure 2:
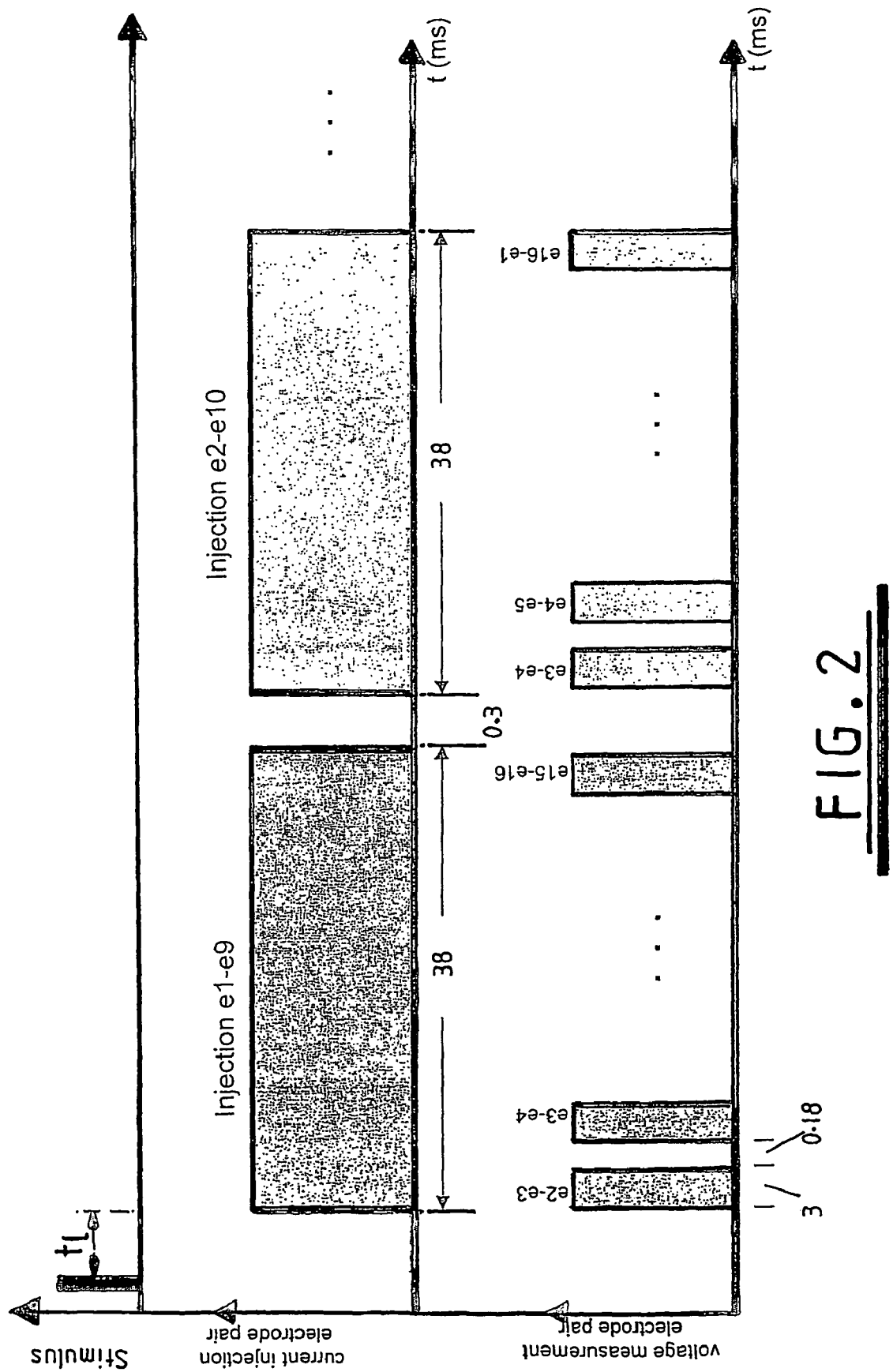
FIG. 2 represents current signals applied and voltage signals measured by the apparatus of FIG. 1.

In use, a stimulus such as a VER stimulus or an AER stimulus is applied to the subject. At a predetermined time after application of the stimulus a current is passed between a first pair of electrodes for a predetermined period. Thereafter current is injected between each pair of electrodes in turn. For each current injection a series of voltage measurements are taken between pairs of electrodes. FIG. 2 comprises three parts, an upper part indicating application of the stimulus (represented by a vertical bar), a central part indicating periods during which current is passed between selected pairs of electrodes, and a lower part indicating periods during which voltage measurements are made between selected pairs of electrodes. Thus, after a time period denoted $t_l$ after application of the stimulus, a start signal is sent from the stimulus generator 6 to the EIT system 4 of FIG. 1. Thus, measurement is triggered at a predetermined time delay after stimulus application. Some embodiments of the EIT system may be configured to commence measurement at a delayed time after receipt of the start signal, and in such cases the time at which the stimulus generator 6 applies the start signal is adjusted accordingly After the start signal is received by the EIT system 4, current is passed between electrodes e1 and e9 for a period of 38 milliseconds. There is then a delay of 0.3 milliseconds, followed by a period of 38 milliseconds during which current is passed between electrodes e2 and e10. During the generation of a single set of measurements, this pattern of current injection is repeated for the following electrode pairs: e1-e9, e2-e10, e3-e11, e4-e12, e5-e13, e6-e14, e7-e15 and e8-e16. During application of current between electrodes e1 and e9, twelve voltage values are measured between adjacent electrodes in sequence, that is electrodes e2-e3, e3-e4, e4-e5, e5-e6, e6-e7, e7-e8, e10-e11, e11-e12, e12-e13, e13-e14, e14-e15, and e15-e16. Some of these measurements are illustrated in the lower part of FIG. 2. No measurements are made between electrode pairs including either of the electrodes (e1 and e9) between which current is passed Each of the voltage measurements is taken over a period of 3.0 milliseconds with a delay of 0.18 milliseconds between successive measurements.

During the first current injection period, the first voltage measurement is taken between electrodes e2 and e3, (electrode e1 being used for current injection) whereas the first voltage measurement during the second current injection period is taken between electrodes e3 and e4 (electrode e2 being used for current injection). The same rolling pattern of electrode selections continues through the full series of eight current injection periods. The EIT system applies a delay of 2 milliseconds between receipt of a signal from the stimulus generator, and initiation of current injection. Thus a full series of measurements is accumulated over a period of 2+8×38+ 7×0.3=308.1 ms.

By applying a stimulus and obtaining a complete set of voltage measurements as described above, an image of the impedance distribution in the brain can be created using known image reconstruction algorithms (see for example "Krylov Subspace Iterative Techniques: on the detection of brain activity with electrical impedance tomography" as referred to above). Such an image can then be viewed by a medical practitioner to determine whether or not the brain has responded to the application of the stimulus in a normal manner. That is, it is known from neurological models which part of the brain should be active at a predetermined $t_l$ value FIG. 2) after application of a particular type of stimulus, and thus the image can be analysed to determine whether or not activity is present as expected in the brain.

The time delay $t_l$ between application of the stimulus and initiation of the EIT measurement process may be variable by a user, using functionality provided by the computer 7 (FIG. 1). Thus, a plurality of images may be generated, by presenting a plurality of stimuli to the user, and initiating EIT measurement at a different $t_l$ value after application of each stimulus. Using this method a plurality of images can be created which can be arranged in order of increasing $t_l$ to represent changing brain activity at different times following application of a stimulus.

In some applications, the computer 7 may be programmed to control the stimulus generator 6 to present the plurality of stimuli, take the necessary measurements at various times after stimulus application, and present the results to the user. In other applications, the computer may be programmed so as to expect a user specified $t_l$ value, apply a stimulus, initiate EIT measurement after the user specified time delay, and create an image using the measurements obtained. Upon reviewing the created image, the user may determine that further images need to be generated at different specific $t_l$ values, and thus further single images can be created.

If the computer 7 is programmed to apply a plurality of stimuli, and generate a plurality of images at different $t_l$ values, delays between successive stimuli are varied in a random manner so as to avoid the subject's brain being "trained" to expect stimuli at particular times. Furthermore, the delay times between different stimuli and the initiation of EIT measurement can be varied in a random manner. Thus images are not generally generated in order of increasing time delay.

Figure 3:
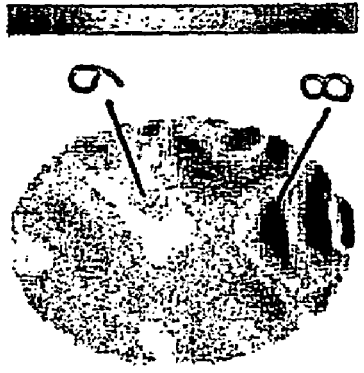
FIG. 3 shows six impedance images generated at various times after the application of a visual stimulus.
Figure 3:
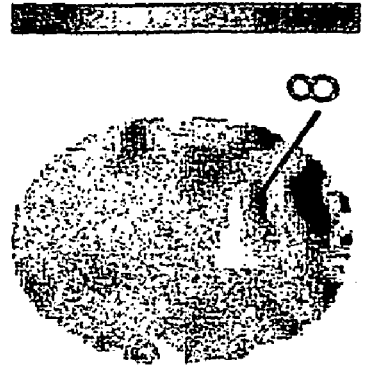
Figure 3:
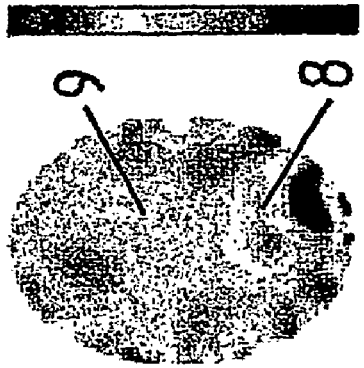
Figure 3:
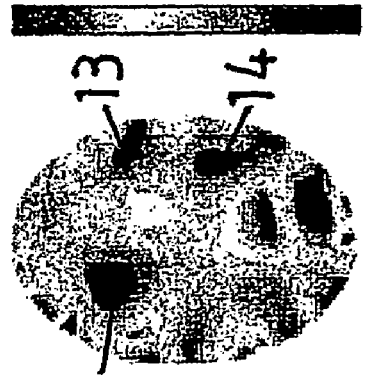
Figure 3:
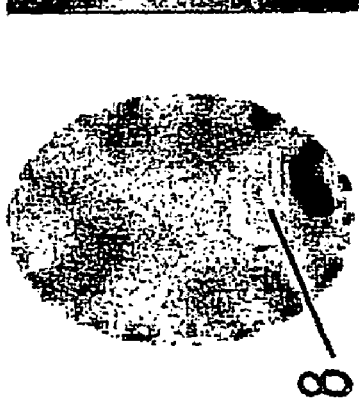
Figure 3:
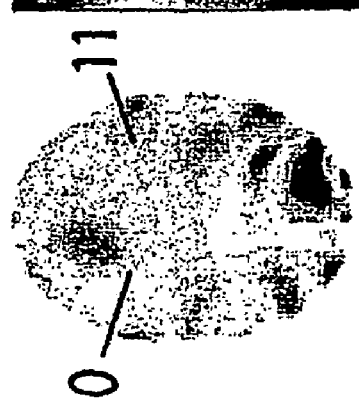

Referring to FIG. 3, there are illustrated six impedance measurements generated at different delays after the application of a visual stimulus. The top left hand image of FIG. 3 was generated by starting EIT measurement at approximately 80 milliseconds after the application of a visual stimulus. The lateral geniculate neucleus (LGN) 8 is shown as being active at the time at which this image was generated. At this time, the LGN was receiving information on brightness and location of the visual stimulus, originating from the rods of the retina. The LGN receives an input from the optic nerve. The LGN is active through most visual processing as can be seen from the six images of FIG. 3.

The upper centre image of FIG. 3 was generated by starting EIT measurement at approximately 105 milliseconds after the application of a visual stimulus. The LGN 8 is still active but at this time neurological modelling shows that information on the colour of the visual stimulus is being processed, originating from the cones of the retina. Brightness and contour information is processed in an area 9 (known as area V1), at the back of the brain. The area 9 is brighter in this image, indicating the expected activity.

The upper right image was generated by staring EIT measurement at 137 milliseconds after the application of a visual stimulus. It can be seen that activity in the area 9 has increased considerably with this part of the brain working to integrate colour stereo and texture information, ready for relay to higher brain regions. In addition, feedback information is being relayed back to the LGN 8 in order to fine tune its processing of future information. Intense activity in LGN area 8 and increased activity in V1 area 9 is indicated in this image.

The lower left image of FIG. 3 was generated by starting EIT measurement at 186 milliseconds after the application of a visual stimulus. It can be seen that information is now being passed to other visual centres 10, 11 at either side of the brain. These areas 10, 11 are responsible for colour processing and the identification of objects.

The lower centre image of FIG. 3 was generated by starting EIT measurement at 201 milliseconds after the application of a visual stimulus. Large dark areas 12, 13, 14 correspond to activity in the left anterior cingulate gyrus and connected regions of the limbic system. These regions are responsible for many things, but most relevant here is the emotion accompanying the recognition of an object. These same regions 12, 13, 14 are responsible for deciding whether a noxious stimulus is actually painful. In the present circumstance, we can assume that these areas of the brain are determining information of the form "that was another flash". It is not surprising that imaging using this technique is able to directly visualise human emotions arising as a result of the sensory stimulus.

The lower right image of FIG. 3 was generated by starting EIT measurement at 248 milliseconds after the application of a visual stimulus. Most visual processing is complete by this stage and higher brain regions are determining the action to be taken in response to the received information. Large parts of the brain are preparing for any subsequent flash, and thus there is a need for random sequences of flashes to eliminate habituation as described above.

The described system could be used to assist in the diagnosis of a patient presenting with blindness. Possible reasons for blindness, caused for example by a blow to the head, include a detached retina or brain damage. Application of a visual stimulus to the patient and examination of an image or images of the patient's brain created using the above-described EIT technique will allow analysis of the cause of blindness. In such examination, a medical practitioner will know where in the brain activity can be expected at particular delay times after stimulus application. If any brain activity is observed, clearly the retina is not detached as signals are being sent to the brain, thus indicating that the blindness may be caused by brain damage. If however no response is observed in the brain to the stimulus, the cause could either be a detached retina, or more serious brain damage. If some brain activity is observed, images can be taken at different delay times after stimulus application, such that images created after a particular time delay do not show expected behaviour. The medical practitioner is therefore provided with an indication of the location of the brain damage.

As a further example, if a patient presents with symptoms of a stroke, an embodiment of the present invention may be used to image brain condition. Electrodes are applied to the patient's head as illustrated in FIG. 1 and as described above. Stimuli are then presented to the patient and response monitored. A nerve stimulator is placed on the patient's leg, and triggered to provide a number of unequally temporally spaced stimuli; at a predetermined time after each stimulus, an EIT measurement is taken creating an image as described above.

When this imaging process is complete, an audio stimulus is provided and a series of images is again created. Similarly, a visual stimulus is provided and a number of images created. The three sets of images created, each in response to a different type of stimulus, allow a thorough assessment of brain function to be made, thus allowing evaluation of the severity of the stroke.

The imaging apparatus required for this procedure is relatively small in size, and relatively cheap to provide. Thus the apparatus may be provided to a general practitioner, allowing him to quickly and easily assess the need for a patient to be referred to a neurologist.

It will be appreciated that although in the described embodiment of the invention each set of measurements is accumulated after a respective stimulating event, all the sets of measurements could be accumulated after a single stimulating event. If the invention is to be implemented in this way, EIT techniques must be used which allow relatively fast current injection and voltage measurement so as to allow images to be captured with the required temporal resolution.

In some embodiments of the present invention, for example those concerned with diagnosing the cause of blindness, only specific parts of the brain need be imaged. By referring to a known neurological model of the brain, the specific parts of the brain that need to be imaged can be identified. Using this information, the number of current injections required can be reduced from the eight injections described with reference to FIG. 2 to one or two carefully selected injections. For example, when imaging the visual pathway current may be passed between regions at the front and the back of the head. That is, injection is parallel to the visual pathway which generally runs from the eyes to the back of the brain. If response to an auditory stimulus is to be monitored, the pathway from the ears to auditory cortex at the side of the brain needs to be monitored, and so electrodes must be placed at least at the side of the head. A parallel voltage measurement protocol may be used. This makes it possible to dramatically reduce the time taken to capture the required measurement data. In alternative embodiments, all current injections described with reference to FIG. 2 may be used, but only a limited number of voltage measurements taken for each injection. Alternatively, both the injections and measurements may be selected on the basis of a neurological model and the applied stimulus.

In the described embodiments, each stimulating event is of short duration. A stimulating event could however be relatively prolonged, extending into a subsequent period during which impedance measurements are made.

It may be desired to use other stimuli occurring in the patient's environment, the application of which cannot be controlled, in place of the deliberate application of stimuli as described above. This is possible, providing accurate timing between occurance of the stimulus and the beginning of EIT frame acquisition process is available.

The measurement data may be processed to reduce sensitivity to effects such as noise and the temporal variation of impedance within the brain during the measurement sequence. For example, a Kalman filter may be used in a conventional manner. In some embodiments of the invention, a plurality of stimulus may be applied, and a number of sets of voltage measurements collected at a particular time after application of each respective stimulus. Sets of voltage measurements collected in this way can then be averaged so as to provide greater accuracy.

What is claimed is:

1. A method for monitoring the response of a nervous system of a body to a sensory stimulus, said method comprising:
   providing a plurality of electrodes on a surface of the body and passing current between selected areas of the surface of the body by passing current between at least one pair of electrodes of said plurality of electrodes, said current being provided by a current source external to said body; and
   collecting a set of voltage measurements between selected ones of said plurality of electrodes while said current is passing between said at least one pair of electrodes;
   wherein the set of voltage measurements is collected over a predetermined measurement period, the predetermined measurement period is initiated after a predetermined delay based upon a neurological model following occurrence of the sensory stimulus, and the collected voltage measurements are compared with reference measurements to determine normal or abnormal response of the nervous system,
   the sensory stimulus comprises a series of second stimuli,
   a set of voltage measurements is collected during current injection periods initiated after application of each second stimulus, the collection of voltage measurements related to each second stimulus is initiated at a time delay relative to the respective second stimulus, and
   the time delay differs for each second stimulus, and differences between collected sets of voltage measurements are interpreted as representing changes in nervous system activity over the time difference between the respective time delays.

2. A method according to claim 1, wherein the set of voltage measurements collected over said measurement period is used to produce an image representing the distribution of impedance within the body.

3. A method according to claim 1, wherein each set of voltage measurements is used to produce a respectively corresponding image representing the distribution of impedance within the body and the thus produced images are compared with each other to identify changes in nervous system activity.

4. A method according to claim 1, wherein the applied sensory stimulus is a visual or an auditory stimulus.

5. A method according to claim 1, wherein measured voltage measurements are filtered using a Kalman filter.

6. A method according to claim 1, further comprising applying the sensory stimulus.

7. A method according to claim 1, wherein when application of the sensory stimulus is detected, said detection starts measurement of said time delay.

8. A method according to claim 7, wherein the sensory stimulus occurs spontaneously.

9. A method according to claim 8, wherein the sensory stimulus is a feature of an environment in which the body is located.

10. A method according to claim 1, wherein said areas are selected on the basis of a neurological model of the nervous system and the applied sensory stimulus such that sensitivity of the derived impedance measurements to changes in a predetermined part of the nervous system is enhanced.

11. A method for monitoring nervous system response to a sensory stimulus, said method comprising:
   (a) applying a predetermined sensory stimulus to a nervous system of a living subject;
   (b) after an initial time delay, injecting electrical current through at least a first pair of electrodes affixed to the head of said subject for a first current injection time period;
   (c) during said first current injection time period, measuring electrical voltage between further pairs of electrodes also affixed to the head of said subject;
   (d) subsequent to said first current injection time period, again injecting electrical current through at least another pair of said electrodes for another current injection time period;
   (e) during said another current injection time period, measuring electrical voltages across other pairs of said electrodes;
   (f) repeating steps (d) and (e) a predetermined number of times;
   (g) creating an image of brain activity in said subject based on said measured electrical voltages;
   (h) repeating steps (a)-(g) for different initial time delays so as to monitor for physiological responses of specific respectively corresponding different parts of the nervous system to derive a time sequence of images revealing nervous system responses to said predetermined sensory stimulus in said corresponding different parts of the subject's brain; and
   (i) outputting said sequence of images to a display.

12. An apparatus for monitoring the response of a nervous system of a body to a sensory stimulus, said apparatus comprising:
   means for providing a plurality of electrodes on a surface of the body and passing current between selected areas of the surface of the body by passing current between at least one pair of electrodes of said plurality of electrodes, said current being provided by a current source external to said body; and
   means for collecting a set of voltage measurements between selected ones of said plurality of electrodes while said current is passing between said at least one pair of electrodes;
   wherein the set of voltage measurements is collected over a predetermined measurement period, the predetermined measurement period is initiated after a predetermined delay based upon a neurological model following occurrence of the sensory stimulus, and the collected voltage measurements are compared with reference measurements to determine normal or abnormal response of the nervous system,
   the sensory stimulus comprises a series of second stimuli, a set of voltage measurements is collected during current injection periods initiated after application of each second stimulus, the collection of voltage measurements related to each second stimulus is initiated at a time delay relative to the respective second stimulus, and
   the time delay differs for each second stimulus, and differences between collected sets of voltage measurements are interpreted as representing changes in nervous system activity over the time difference between the respective time delays.

13. An apparatus according to claim 12, wherein each set of voltage measurements is used to produce a respectively corresponding image representing the distribution of impedance within the body and the thus produced images are compared with each other to identify changes in nervous system activity.

14. An apparatus according to claim 12, wherein the applied sensory stimulus is a visual or an auditory stimulus.

15. An apparatus according to claim 12, wherein measured voltage measurements are filtered using a Kalman filter.

16. An apparatus according to claim 12, further comprising applying the sensory stimulus.

17. An apparatus according to claim 12, including means for detecting application of the sensory stimulus to start measurement of said time delay.

18. An apparatus according to claim 17, wherein the sensory stimulus occurs spontaneously.

19. An apparatus according to claim 18, wherein the sensory stimulus is a feature of an environment in which the body is located.

20. An apparatus according to claim 12, wherein said areas are selected on the basis of a neurological model of the nervous system and the applied sensory stimulus such that sensitivity of the derived impedance measurements to changes in a predetermined part of the nervous system is enhanced.

21. An apparatus according to claim 12, including means for using the set of voltage measurements collected over said measurement period to produce an image representing the distribution of impedance within the body.

22. An apparatus for monitoring nervous system response to a sensory stimulus, said apparatus comprising:
   (a) means for applying a predetermined sensory stimulus to a nervous system of a living subject;
   (b) means for, after an initial time delay, injecting electrical current through at least a first pair of electrodes affixed to the head of said subject for a first current injection time period;
   (c) means for, during said first current injection time period, measuring electrical voltage between further pairs of electrodes also affixed to the head of said subject;
   (d) means for, subsequent to said first current injection time period, again injecting electrical current through at least another pair of said electrodes for another current injection time period;
   (e) means for, during said another current injection time period, measuring electrical voltages across other pairs of said electrodes;
   (f) means for repeatedly using means (d) and (e) a predetermined number of times;
   (g) means for creating an image of brain activity in said subject based on said measured electrical voltages;
   (h) means for repeatedly using means (a)-(g) for different initial time delays so as to monitor for physiological responses of specific respectively corresponding different parts of the nervous system to derive a time sequence of images revealing nervous system responses to said predetermined sensory stimulus in said corresponding different parts of the subject's brain; and
   (i) means for outputting said sequence of images to a display.

* * * * *